United States Patent
Cochet et al.

(10) Patent No.: US 10,345,286 B2
(45) Date of Patent: Jul. 9, 2019

(54) METHOD TO DETERMINE A CETANE NUMBER OF A FUEL

(71) Applicant: DELPHI TECHNOLOGIES IP LIMITED, St. Michael (BB)

(72) Inventors: Thierry Cochet, Molineauf (FR); Jean-Michel Bacq, Charge (FR)

(73) Assignee: DELPHI TECHNOLOGIES IP LIMITED (BB)

( * ) Notice: Subject to any disclaimer, the term of this patent is extended or adjusted under 35 U.S.C. 154(b) by 111 days.

(21) Appl. No.: 15/516,099

(22) PCT Filed: Sep. 29, 2015

(86) PCT No.: PCT/EP2015/072377
§ 371 (c)(1),
(2) Date: Mar. 31, 2017

(87) PCT Pub. No.: WO2016/050744
PCT Pub. Date: Apr. 7, 2016

(65) Prior Publication Data
US 2017/0299568 A1    Oct. 19, 2017

(30) Foreign Application Priority Data
Oct. 1, 2014   (GB) .................................... 1417304.1

(51) Int. Cl.
*F02P 5/00*       (2006.01)
*G01N 33/28*      (2006.01)
*F02D 41/00*      (2006.01)
*F02D 41/14*      (2006.01)
*F02D 19/06*      (2006.01)
(Continued)

(52) U.S. Cl.
CPC ..... *G01N 33/2829* (2013.01); *F02D 19/0636* (2013.01); *F02D 19/0649* (2013.01); *F02D 41/0087* (2013.01); *F02D 41/123* (2013.01); *F02D 41/1497* (2013.01); *F02D 41/401* (2013.01); *F02D 2200/0612* (2013.01); *F02D 2200/101* (2013.01); *Y02T 10/36* (2013.01); *Y02T 10/44* (2013.01)

(58) Field of Classification Search
CPC .. F02P 5/00; F02P 5/045; F02P 5/1504; F02P 5/1521; F02P 5/1522
USPC .................. 123/406.47, 406.48, 568.21, 445
See application file for complete search history.

(56) References Cited

U.S. PATENT DOCUMENTS 4,397,285 A * 8/1983 O'Neill ................... F02D 1/183
                                                   123/435
7,621,174 B2  11/2009 Takaku
(Continued)

*Primary Examiner* — John Kwon
(74) *Attorney, Agent, or Firm* — Joshua M. Haines

(57) ABSTRACT

A method of determining the cetane number of a fuel in an internal combustion engine comprising, during running of the engine, i) with respect to one cylinder, performing a routine including a series of injections such that for each injection a quantity of fuel is injected into the cylinder, and during the routine varying the angle at which the injections takes place with respect to crankshaft angle; ii) measuring engine speed at intervals during the series of injections and determining values for changes in engine speed consequent to the injections; iii) determining cetane number from a pre-stored relationship relating the cetane number to changes in engine speed consequent to changes in the test injection angle.

12 Claims, 2 Drawing Sheets

(51) Int. Cl.
 *F02D 41/12* (2006.01)
 *F02D 41/40* (2006.01)
 F02B 47/08 (2006.01)

(56) References Cited

U.S. PATENT DOCUMENTS

| | | |
|---|---|---|
| 8,281,643 B2 | 10/2012 | Yasuda |
| 8,538,664 B2 | 9/2013 | Miyaura et al. |
| 2007/0012289 A1* | 1/2007 | Yamaguchi ........... F02D 35/028 123/406.47 |
| 2009/0198456 A1 | 8/2009 | Tsutsumi et al. |
| 2010/0236524 A1* | 9/2010 | Bohnig ............... F02D 41/0025 123/445 |

* cited by examiner

METHOD TO DETERMINE A CETANE NUMBER OF A FUEL

CROSS REFERENCE TO RELATED APPLICATIONS

This application is a national stage application under 35 USC 371 of PCT Application No. PCT/EP2015/072377 having an international filing date of Sep. 29, 2015, which is designated in the United States and which claimed the benefit of GB Patent Application No. 1417304.1 filed on Oct. 1, 2014 the entire disclosures of each are hereby incorporated by reference in their entirety.

FIELD OF THE INVENTION

This disclosure relates to a method of determining the cetane number of a fuel. It has particular but not exclusive application to determine cetane numbers in standard Diesel engines.

BACKGROUND

The cetane number of a fuel (e.g. Diesel) provides a measure of the ignition characteristics when used in compression ignition engines. The cetane number scale ranges from 0 to 100, but is typically tested in the range 30 to 65.

It is useful to know the cetane number of a fuel in order to provide the most efficient combustion in modern diesel engines that have low compression ratios. Modern diesel engines are quite sensitive to fuel with cetane numbers below 50.

In order to determine cetane number, traditionally a standard testing technique uses a standard single cylinder of a four stroke cycle Diesel engine having a variable compression ratio. The principle behind this technique is to determine the compression ratio that corresponds to a predefined auto ignition delay. The auto ignition delay is determined by measuring, during the combustion cycle, two different times. The first when the injector injects the fuel and the second when the combustion starts. The difference of these two times gives the auto ignition delay.

In this manner, cetane number and compression ratio are related using a calibration curve, and the cetane number can be determined. The calibration utilises the points from alpha-methylnapthalene and n-cetane that are arbitrarily assigned to cetane numbers 0 and 100.

The above procedure requires a special engine and cannot be performed on a standard diesel engine. It is an object of the invention to determine cetane number using a standard engine and furthermore without the use of additional sensors.

STATEMENT OF THE INVENTION

According to one aspect is provided a method of determining the cetane number of a fuel in an internal combustion engine comprising, during running of the engine, i) with respect to one cylinder, performing a routine comprising a series of injections wherein for each injection a quantity of fuel is injected into said cylinder, and during said routine varying the angle at which said injections takes place with respect to crankshaft angle; ii) measuring engine speed at intervals during said series of injections and determining values for changes in engine speed consequent to said injections; iii) determining cetane number from a pre-stored relationship relating said cetane number to changes in engine speed consequent to changes in said test injection angle.

Preferably the method includes filtering the values from step ii).

Preferably for a said test injection, said change in engine speed is defined as the change in engine speed consequent to said injection from a previously measured engine speed which is subsequent to the previous test injection.

Preferably step ii) includes further modifying said values by a factor so as to be dependent only on the injected fuel quantity and wherein step iii) comprises determining cetane number from a pre-stored relationship relating said cetane number to correspondingly modified changes in engine speed consequent to changes in said test injection angle.

Preferably the method comprises further normalising said values or modified values of step ii) to provide normalised values or modified values which are dimensionless, and step iii) comprises determining cetane number from a pre-stored relationship relating said cetane number to corresponding normalised changes/modified changes in engine speed consequent to changes in said test injection angle.

Preferably said normalisation comprises dividing said values/modified values by the equivalent value/modified value of speed change at a particular timing angle.

Said injection is preferably performed during each engine cycle.

Preferably no fuel is injected into other cylinders during said sweep routine.

Preferably said test injection is performed at a different crankshaft angle in consecutive engine cycles.

Preferably the timing of the injections with respect to the crankshaft angle are increased or decreased monotonically.

Preferably the said routine is performed during deceleration; power off or fuel cut off conditions.

BRIEF DESCRIPTION OF DRAWINGS

The invention will now be described with reference to the following figures of which.

DESCRIPTION OF EMBODIMENTS

Figure 1:
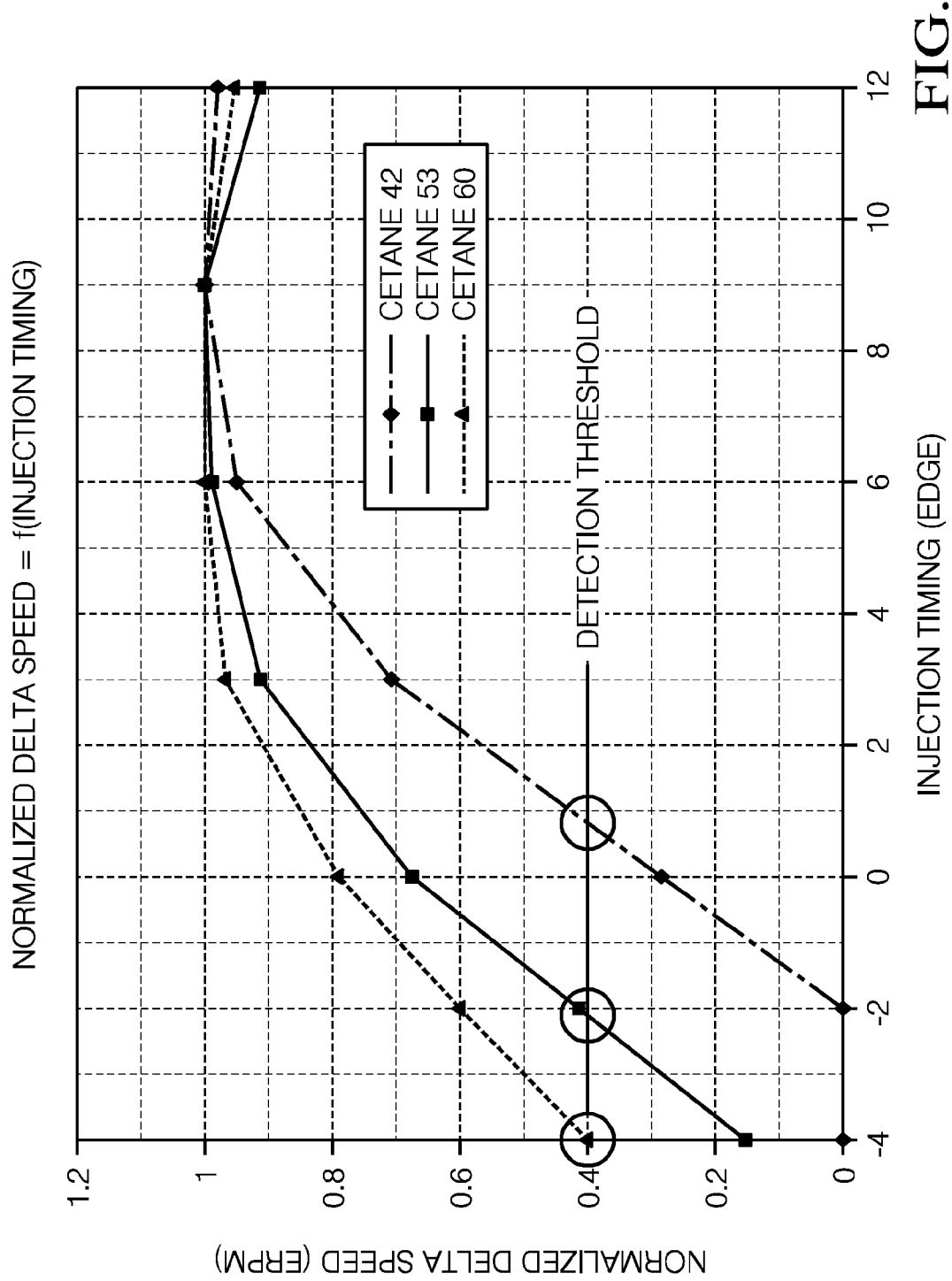
FIGS. 1 and 2 show graphs relating normalised delta (engine) speed to the angle of injection of a test injection in one cylinder during testing process for fuels having varying cetane numbers.

In general, in one example the methodology monitors engine speed, and processes this parameter for specific injection sequences, and uses this to determine cetane number (e.g. by looking at differences in engine speed with particular injection sequences).

In particular methodology a test method is performed wherein a series of test injections are performed with respect to one injector (cylinder) only, and where the same quantity of fuel is injected. During the injections the angle (with respect to the crankshaft) is varied. So for example the process in one example can be regarded as performing a timing sweep. In this fuel is injected with respect to one cylinder over an angle X1 degrees to X2 degrees using increments of y degrees. So for example from +8 to −8 degrees relative to TDC; so then the test is performed is a series of (adjacent engine cycles) where for the test cylinder fuel is injected at a particular crankshaft angle relative to Top Dead Centre). Of course the timing sweep may be started at any angle but preferably a small angle before TDC.

The timing sweep process may be performed where the test injection is performed at the same angle for a plurality of engine cycles rather than varying at each cycle, but is preferably performed wherein the angle is changed after each engine cycle.

The method is preferably performed during the following conditions, i.e. at the following times: after each tank refueling; during deceleration; fuel cut off when the engine is hot enough and/or at a specific fuel rail pressure.

Also during this time, fuel is preferably not injected into the other cylinders. Thus the test sequence is performed preferably during deceleration (foot off conditions).

The testing preferably is initialised with a number (e.g. 7) of shots (i.e. 7 engine cycles) without any injection at all—there is no test injection in the test cylinder at all (or other cylinders). This initial step is preferably performed in order to adjust the zero of the monitored signal. So for example in a deceleration condition there is no injection.

During the main testing process (timing sweep), a sequence of N shots is performed (thus for N engine cycles where, for the test cylinder, there is a test injection whose timing is set different values of injection angle). The filtered difference of engine speed subsequent to the injection is measured for each, timing is calculated, and recorded for each shot. Again timing means the injection position in engine degree relative to TDC.+10 degrees of timing means a fuel injection 10 degrees before top dead centre.

In an alternative there may be a sequence of a number of shots at the same angle (e.g. +8 degrees), engine speed measurements taken and the average speed determined; this is then repeated at changing angles, i.e. repeated shots at another angle, then repeat for another angle. This has the advantage that opposed to the variation of angle was made for each consecutive shot, there is more time for the system to adjust and thus more accurate results may be obtained. A disadvantage however is that the sequence duration will be increased and could be too long to be performed during a deceleration.

As mentioned a filtered difference of engine speed (consequent to injection) is measured i.e. the difference in speed at a point before the injection and subsequent to injection is determined.

The skilled person would be aware that the times at which the two speeds are measured to determine the difference (before and after injection) can be any appropriate times, and/or may be averaged. In one example the times may be to a particular timing angle subsequent to injection, and from a time at particular point prior to injection; e.g. the same timing angle but respect of the previous cylinder. Thus, in the later example:

Delta speed=HPF_engine_speed($N$)−HPF_engine_speed($N$−1) where

HPF=High Pass Filtered N=test cylinder and N−1=cylinder just before test cylinder.

These high pass filtered engine speeds will be used to calculate change in speed; referred to here as delta speed.

In one example, for a 4-stroke engine the engine speed is measured (and filtered) over portions of the engine cycle for each cylinder. So for a 4 cylinder engine (engine cycle lasts over a 720 degrees of crankshaft rotation), engine speed is measured on 180 engine degrees. Then we have one engine speed by cylinder. 4 engine speeds for a 4 cylinder engine.

Engine speed difference is also referred to as "delta speed". As mentioned preferably high pass filtration is applied on these engine speeds in order to remove the low frequency and keep the high frequency (a peek of engine speed) generated by the combustion on the test cylinder.

Delta speed is function of the fuel injected quantity, the rail pressure, and the engine speed.

In a further preferred embodiment in order to only depend on fuel injected quantity, Delta speed can be divided by a factor. This factor is dependent on fuel pressure, engine speed and can be provided by a map e.g. stored in the computer. Such a MAP and values can be determined by appropriate testing and it would be clear to the skilled person how such a MAP of these values can be provided.

Modified (SPC) delta speed=Delta speed/map(fuel pressure, engine speed)

Then SPC delta speed will only depend on fuel injected quantity.

A further step is to provide a parameter that depends only on injection timing and not fuel injected quantity. In one example this parameter is referred to as Normalised Delta Speed, and is determined (for each angle e.g. x degrees) relative to the SPC delta speed at a particular angle e.g. the angle at the start of the sweep e.g. +8 degrees:

Normalised Modified (SPC) Delta Speed (at $x$ degrees)=(modified (SPC) delta speed at $x$ degrees/modified (SPC) delta speed at 8 degrees).

To improve the signal quality, a low pass filtration may be preferably applied.

By using a normalised delta speed there is no need to have a good accuracy on the injected pilot quantity e.g. if there is slow variation in injected quantity.

So normalised Delta Speed=f(injection timing). FIG. 1 shows normalised delta speed plotted against as a function of pilot injection timing—i.e. FIG. 1 shows how the normalised delta speed determined from the above procedure varies as a function of the timing of when the test injection is made, and also, as can be seen, as a function of cetane number (the plots vary with differing cetane numbers).

The horizontal line shows a particular normalised delta speed and shows how for this particular value (in this case 0.4) is achieved at particular injection timings depending on the cetane number. The timing that corresponds to the late combustion (poor combustion efficiency) is found as the intersection between a detection threshold and the curve.

Combustion efficiency is dependant on injection timing and cetane number (as described on the following graph). However for a normalized delta speed of 1, the cetane number effect is not visible. For a smaller normalized delta speed of 0.4, the cetane number effect is more visible.

Figure 2:
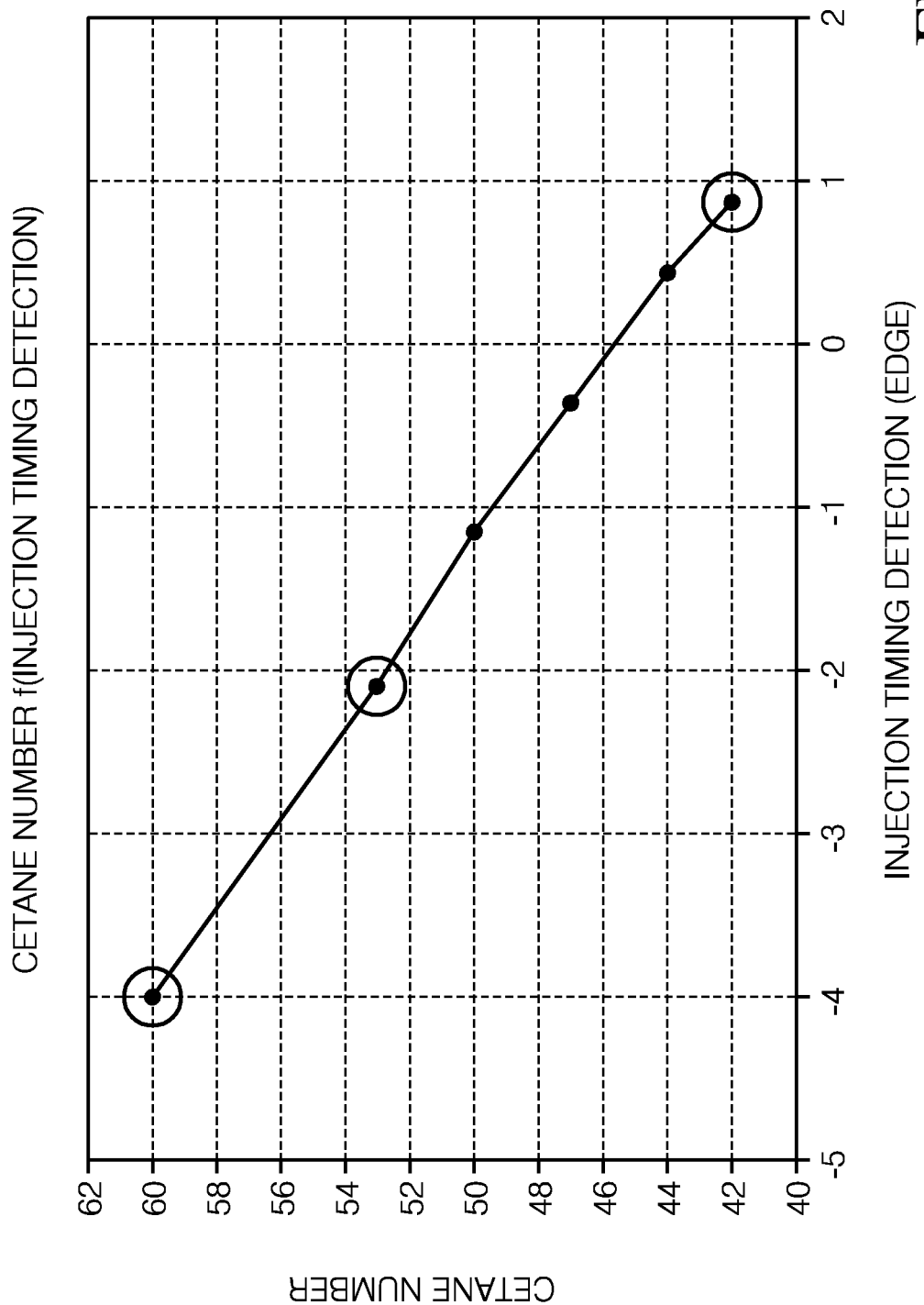

FIG. 2 shows a graph relating the cetane number to the injection timing at a particular pre-set (nominal) normalised delta speed. Thus such a map may be stored in the ECU and read after the above procedure to determine cetane number.

In a preferred embodiment other factors are taken into account. For a given engine the timing will not only be dependent on cetane number but also on air pressure and temperature conditions. Thus in a preferred embodiment the biasing effects of these is taken into consideration. The effects of such biases can be determined from engine testing at differing air pressures and temperatures with different cetane numbers. Such biasing effects can be saved for example in maps in an engine ECU.

The invention claimed is:

1. A method of determining the cetane number of a fuel in an internal combustion engine, during running of the engine, the method comprising the steps of:

i) with respect to one cylinder, performing a routine comprising performing a series of injections wherein for each injection a quantity of fuel is injected into said one cylinder, and during said routine varying the angle at which said injections takes place with respect to crankshaft angle;

ii) measuring engine speed at intervals during said series of injections and determining values for changes in engine speed consequent to said series of injections; and iii) determining a cetane number from a pre-stored relationship relating said cetane number to said changes in engine speed;

said method further comprising normalising said values of step ii) to provide normalised values or modified values which are dimensionless, and step iii) comprises determining cetane number from a pre-stored relationship relating said cetane number to said values that have been normalized.

2. A method as claimed in claim 1 including filtering the values from step ii).

3. A method as claimed in claim 1 wherein for a given injection of said series of injections, a given change in engine speed of said changes in engine speed is defined as the difference in engine speed consequent to said give injection from a previously measured engine speed which is subsequent to the previous injection of said series of injections.

4. A method as claimed in claim 1 wherein step ii) further includes modifying said values by a factor so as to be dependent only on the injected fuel quantity and wherein step iii) comprises determining cetane number from a pre-stored relationship relating said cetane number to said values modified by a factor.

5. A method as claimed in claim 4 further comprising normalising said modified values of step ii) to provide normalised modified values which are dimensionless, and step iii) comprises determining cetane number from a pre-stored relationship relating said cetane number to said normalized modified values.

6. A method as claimed in claim 5 wherein said normalizing comprises dividing said modified values by the equivalent modified value of speed change at a particular timing angle.

7. A method as claimed in claim 1 wherein said normalizing comprises dividing said values by the equivalent value of speed change at a particular timing angle.

8. A method as claimed in claim 1 wherein one injection of said series of injections is performed during each engine cycle.

9. A method as claimed in claim 1 wherein no fuel is injected into other cylinders during said routine.

10. A method as claimed in claim 1 wherein consecutive injections of said series of injections are performed at different crankshaft angles in consecutive engine cycles.

11. A method as claimed in claim 1 wherein the timing of said series of injections with respect to the crankshaft angle are increased or decreased monotonically.

12. A method as claimed in claim 1 wherein said routine is performed during deceleration; power off or fuel cut off conditions.

* * * * *